United States Patent
LeGette et al.

[11] Patent Number: 5,835,609
[45] Date of Patent: Nov. 10, 1998

[54] EAR PROTECTION DEVICE

[75] Inventors: Brian E. LeGette, Severna Park, Md.; Ronald L. Wilson, II, Vienna, W. Va.

[73] Assignee: The Gorgonz Group, Inc., Naperville, Ill.

[21] Appl. No.: 676,597

[22] Filed: Jul. 3, 1996

Related U.S. Application Data

[63] Continuation-in-part of Ser. No. 450,587, Jun. 2, 1995, abandoned.

[51] Int. Cl.⁶ .................................................... H04R 25/00
[52] U.S. Cl. ............................................... 381/187; 2/209
[58] Field of Search ........................... 381/25, 183, 187, 381/205; 379/430; 181/129, 130, 137; 128/866, 864, 857; 2/209, 906

[56] References Cited

U.S. PATENT DOCUMENTS

| | | |
|---|---|---|
| 548,738 | 10/1895 | Ballard . |
| 1,179,473 | 4/1916 | Taylor . |
| 1,326,875 | 12/1919 | Miller . |
| 1,398,958 | 12/1921 | Basch .......................................... 2/209 |
| 1,628,483 | 5/1927 | Wiegand et al. . |
| 2,070,216 | 2/1937 | Rosenberg .................................. 2/209 |
| 2,246,031 | 6/1941 | Baritz et al. ................................ 2/209 |
| 2,314,782 | 3/1943 | Goretsky ..................................... 2/209 |
| 2,532,852 | 12/1950 | Oaks ....................................... 128/151 |
| 2,586,644 | 2/1952 | Gilbert .................................... 381/183 |
| 2,615,169 | 10/1952 | Maxant et al. . |
| 2,671,221 | 3/1954 | Triplette .................................... 2/208 |
| 2,717,930 | 9/1955 | Hintz ....................................... 381/183 |
| 3,249,949 | 5/1966 | Rosenberg et al. ......................... 2/209 |
| 3,308,480 | 3/1967 | Elder ......................................... 2/209 |
| 3,447,160 | 6/1969 | Teder ......................................... 2/209 |
| 3,509,580 | 5/1970 | Rubenstein et al. .......................... 2/65 |
| 3,787,899 | 1/1974 | Krawagna .................................. 2/209 |
| 4,277,847 | 7/1981 | Florio ......................................... 2/12 |
| 4,404,434 | 9/1983 | Pelt et al. ............................. 179/156 R |
| 4,463,223 | 7/1984 | Yamanoi et al. ..................... 179/156 R |
| 4,516,274 | 5/1985 | Buckland .................................... 2/209 |
| 4,546,215 | 10/1985 | Ferraro ................................ 179/156 R |
| 4,654,898 | 4/1987 | Ishikawa ..................................... 2/209 |
| 4,669,129 | 6/1987 | Chance ........................................ 2/209 |
| 4,670,911 | 6/1987 | Dunford ...................................... 2/209 |

(List continued on next page.)

FOREIGN PATENT DOCUMENTS

| | | |
|---|---|---|
| 0 745 364 A3 | 3/1996 | European Pat. Off. . |
| 1353524 | of 1964 | France . |
| 2 536 253 | 11/1982 | France . |
| 2 532 838 | 9/1983 | France . |
| 294003 | 1/1954 | Sweden . |

OTHER PUBLICATIONS

Advertisement: The "PODS" ear warming eye glass retainer, Shred Alert Products of Hood River, Oregon.

*Primary Examiner*—Huyen Le
*Attorney, Agent, or Firm*—Kenyon & Kenyon

[57] ABSTRACT

There is provided an ear covering device to be worn over the ears of the individual and to extend around the back of the individual's head or neck. The covering device is formed by a frame having a flexible band and two ear cups on each end. The band is contemplated to be flexible so that the space between opposite ear cup members may be enlarged to permit attachment of the covering device onto the back of the head. The spring force of the flexible band causing engagement of the covering device over the ears of the individual with the flexible band wrapping around the back of the individual's head or neck. Each ear cup includes a frusto conical frame portion having a central opening therein. Fabric covers the frusto conical portion of the ear cups as well as the flexible band. The frusto conical frame along with the fabric cover form a pocket. Suitable materials are provided in order to create a comfortable feeling, as well as provide warmth and protection for the ears. Earphones may be inserted into the pocket to create a combination ear protection device and headphone. The ear cups may also be hingedly attached to the band to permit collapsing of the covering device when not in use.

26 Claims, 10 Drawing Sheets

U.S. PATENT DOCUMENTS

| | | | |
|---|---|---|---|
| 4,727,599 | 2/1988 | Rappaport et al. | 455/351 |
| 4,776,042 | 10/1988 | Hanson et al. | 2/7 |
| 4,776,044 | 10/1988 | Makins | 2/199 |
| 4,791,684 | 12/1988 | Schwartz | 2/209 |
| 4,858,248 | 8/1989 | Goldsmith et al. | 2/209 |
| 4,864,619 | 9/1989 | Spates | 381/25 |
| 4,918,757 | 4/1990 | Janssen et al. | 2/171 |
| 4,982,451 | 1/1991 | Graham | 2/906 |
| 5,038,412 | 8/1991 | Cionni | 2/209 |
| 5,117,464 | 5/1992 | Jones et al. | 381/183 |
| 5,164,987 | 11/1992 | Raven | 381/25 |
| 5,201,856 | 4/1993 | Edwards | 2/209 |
| 5,257,420 | 11/1993 | Byrne, Jr. | 2/209 |
| 5,327,178 | 7/1994 | McManigal | 351/158 |
| 5,339,467 | 8/1994 | Brinkley | 2/209 |

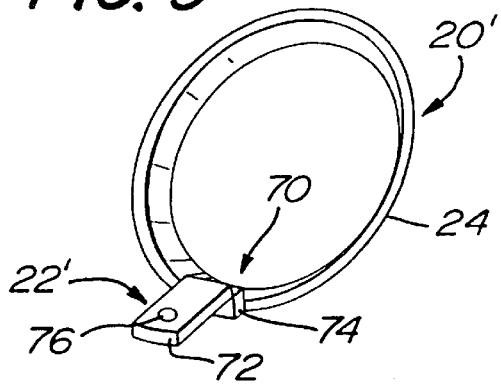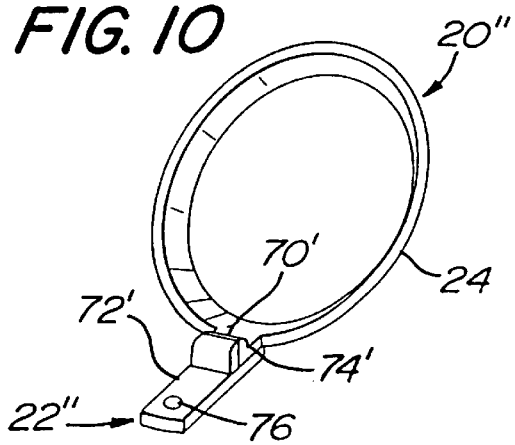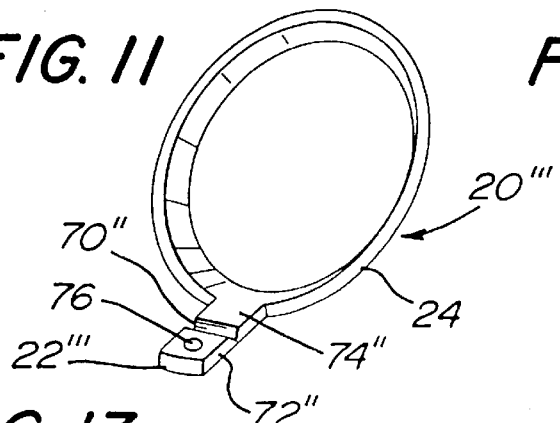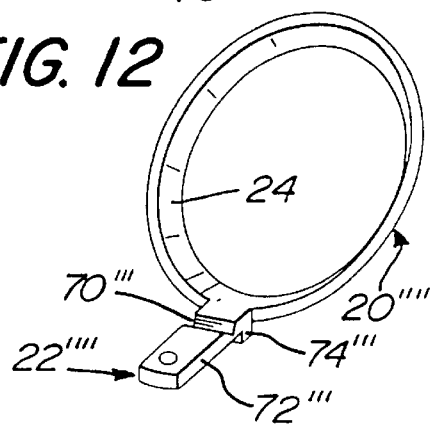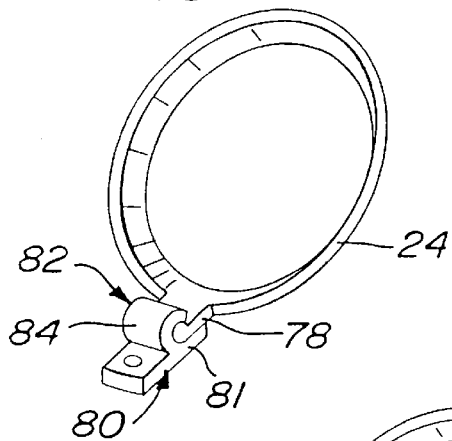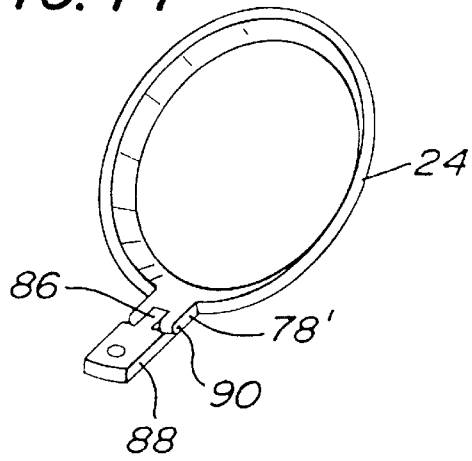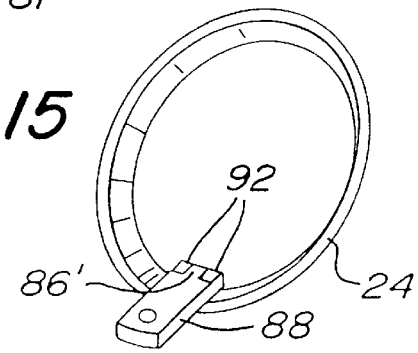

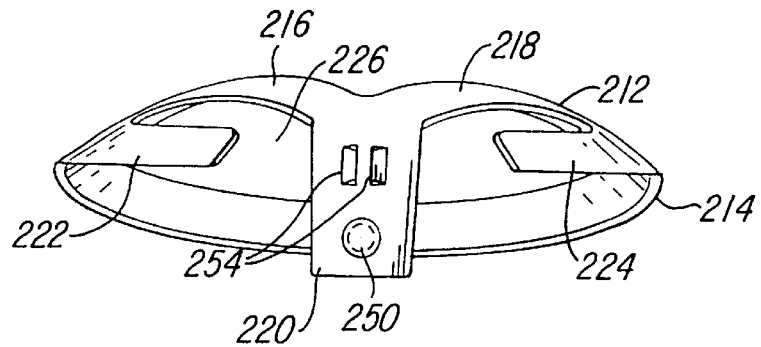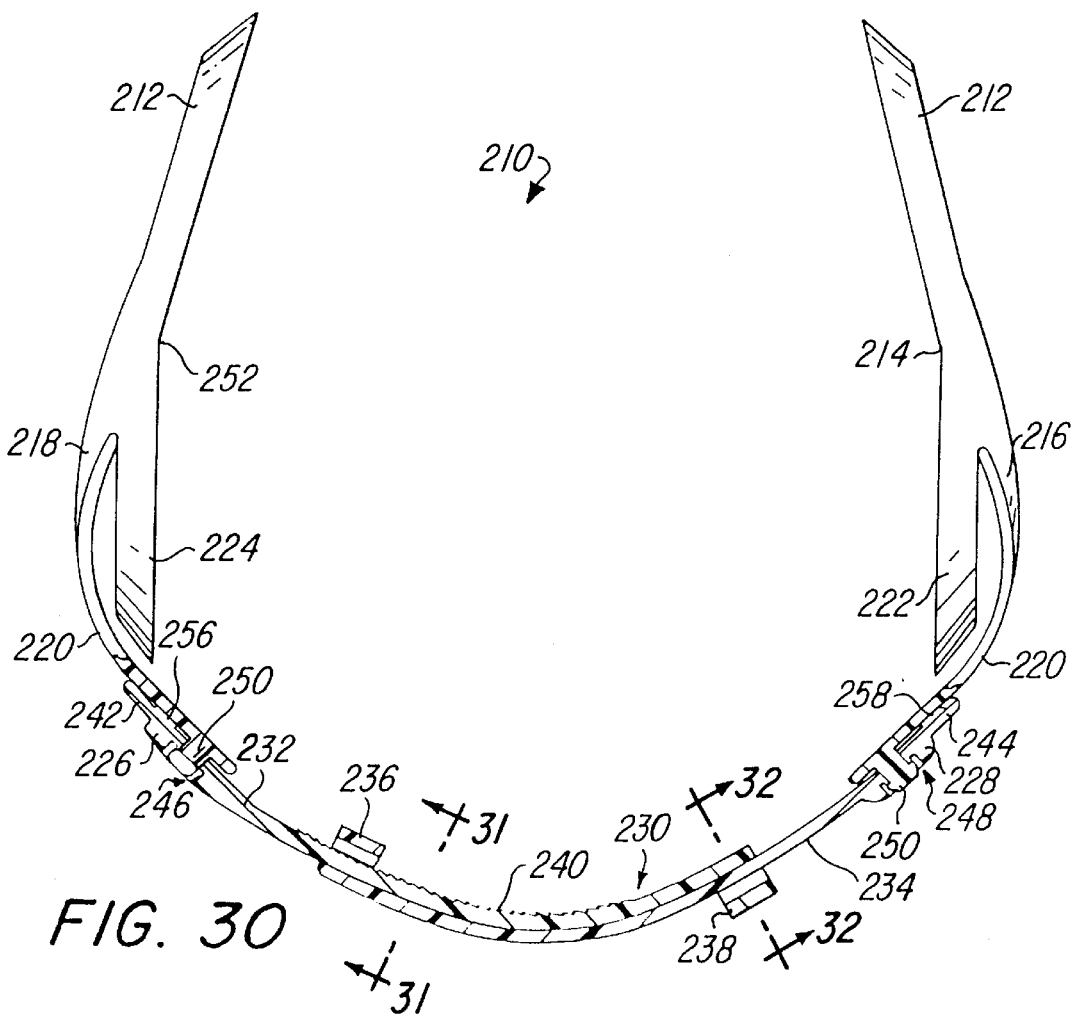

EAR PROTECTION DEVICE

CROSS REFERENCE TO RELATED APPLICATION

This is a continuation-in-part of copending application Ser. No. 08/460,587 which was filed Jun. 2, 1995.

FIELD OF THE INVENTION

The present invention relates to a covering to be worn over and to protect the ears of an individual. The covering is intended to extend around the back of the head or neck of the individual when being worn. The present invention also relates to an ear protection device that may incorporate audio earphones or similar type elements.

BACKGROUND OF THE INVENTION

There are a number of prior devices which cover an individual's ears for warmth or the like. These devices, generally known as "ear muffs", are represented in part by U.S. Pat. No. 3,249,949 to Rosenberg et al. and U.S. Pat. No. 3,509,580 to Rubenstein et al. These prior ear muffs generally include a band which wraps around the top of the head and includes an enlarged end which engages and covers the ears for warmth and protection.

An alternate method for securing ear protection type structures is shown in Rosenberg U.S. Pat. No. 2,070,216 which is in the form of a headband. Edwards U.S. Pat. No. 5,201,856 shows a device which wraps around the side of an individual's head and attaches at the front end to the arms of eyeglasses. Brinkley U.S. Pat. No. 5,339,467 shows an ear protection type device which attaches to the rim of the ear and maintains its position without a securing strap or the like.

Ballard U.S. Pat. No. 548,738 shows an ear and neck protecting device which wraps around the back of the individual's head and covers the neck to a position below the collar. Triplett U.S. Pat. No. 2,671,221 shows an ear protection device that wraps around the back of an individual's head and includes a hinge at its center.

It has previously been contemplated that audio speakers may be incorporated into ear muff or headband type devices. Krawangna U.S. Pat. No. 3,787,899 shows an ear muff that includes audio speakers therein. Spates U.S. Pat. No. 4,864,619 shows a stereo head set within a headband. A wrap for a standard headphone is shown in Byrne, Jr. U.S. Pat. No. 5,257,420.

Despite the existence of various types of ear muffs and headbands, there remains a need for an ear protection device having the advantages of the present invention.

SUMMARY OF THE INVENTION

The present invention relates to a covering device to be worn over the ears of an individual. Preferably, the covering device extends between the opposite ears around the back of the individual's head or neck.

One embodiment of the covering device of the present invention includes a flexible band which is positioned between two ear cups. The band includes a central curved portion and two end portions. The ear cups are attached to the end portions of the band and project therefrom. At least one portion of the ear cups includes a frusto conical frame member having a central opening therein. A fabric is used to cover at least the frusto conical portion and central opening of the ear cups so as to form a covering for the ears.

The fabric which covers the ear covering device may cover both the ear cups and the band. The fabric may include an opening within the portion covering the ear cups so that a earphone or the like may be inserted into the pocket formed by the frusto conical frame portion and the fabric covering. The ear cups may also be hingedly connected to the ends of the band and the band may be collapsible.

Another embodiment of the covering device of the present invention includes a band having two curved portions with one end of each curved band portion overlapping and slideably attached to the other curved band portion such that the relative overall length of the band may be adjusted. Two ear cup portions are attached to the free ends of the curved portions. The ear cups may include V-shaped support flanges. A semi-circular frame extends between the projections of the V-shaped portion. A curved ear cup extension portion extends from each of the projections of the V-shape in a direction opposite of the semi-circular portion. These portions of the ear cup form an ear cavity. The semi-circular portion and the support flanges also define a central opening in the ear cavity. An attachment flange projects from the vertex of the V-shaped support flanges. The attachment flange including means thereon for rotatably attaching the ear cups to the free ends of the curved band portions. Fabric means covers the band and the ear cups on both sides and forms a pocket adjacent the central opening in the ear cups.

The invention further contemplates the use of specific dimensional relationships between the ear cups and the band, as well as specific materials for the construction of the covering device, so as to form a comfortable and functional ear covering device which may be worn by almost any individual for protection of the ears.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIGS. 9 through 15 show various embodiments of a hinged connection for use with the ear covering device of the present invention.

FIG. 29 is a side elevation of the alternate embodiment of the ear covering device as shown in FIG. 28.

FIG. 30 shows a side elevation of the alternate frame embodiment as contemplated by FIGS. 28 and 29.

DETAILED DESCRIPTION OF THE INVENTION

Figure 1:
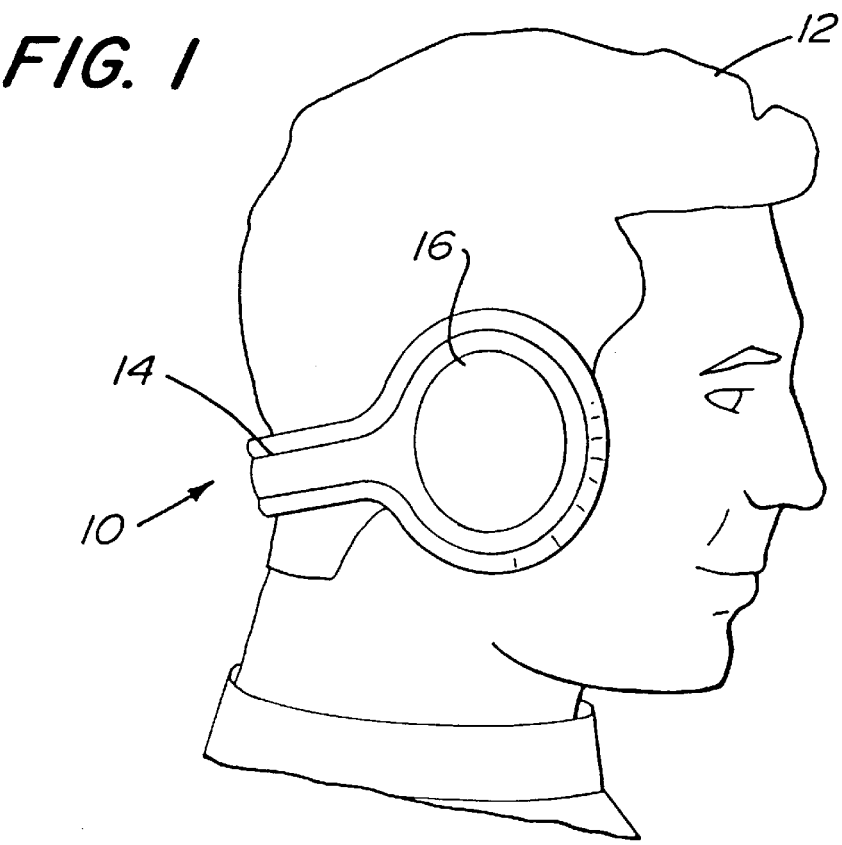
FIG. 1 shows one form of the covering device contemplated by the present invention as being worn by an individual.

In the Figures, where like numerals indicate like elements, there is shown multiple forms of an ear covering device as contemplated by the present invention. The ear covering device as illustrated in FIG. 1 is generally designated by the numeral 10. The ear covering device 10 is adapted to be worn over the ears of an individual 12. When worn, the device 10 extends around the back of the head and/or neck of the wearer.

The ear covering device 10 generally includes a band portion 14 and two ear protecting portions 16. One side of the ear covering device 10 is illustrated in FIG. 1. The opposite side of device 10 is contemplated to be a mirror image of that illustrated in FIG. 1. As illustrated in FIG. 1, the band portion 14 is relatively narrower than the ear covering portions 16. It is contemplated that variations on this dimensional relationship may be made without departing from the essence of the present invention.

Figure 2:
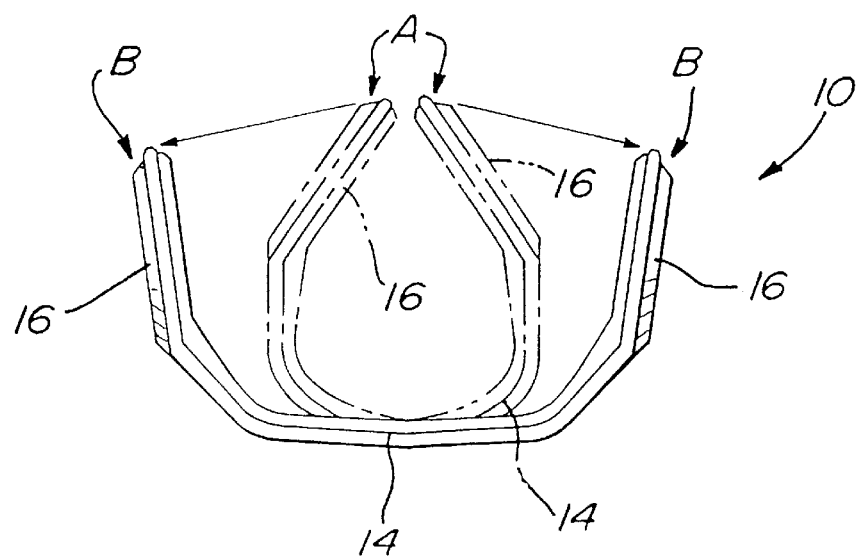
FIG. 2 shows a top elevational view of an ear covering device contemplated by the present invention.

FIG. 2 shows a top plan view of the ear covering device 10 illustrated in FIG. 1. In position "A" in FIG. 2, the ear covering device 10 is illustrated in its normal rest position with the ear covering portions 16 positioned closely adjacent to one another. The rest positioning of the covering portions is created by the curvature of band portion 14 and the form of the frame for the ear covering portions 16 (shown in detail in other figures). Position "B", as illustrated in FIG. 2, shows the ear covering portions 16 deflected outwardly due primarily to a flexing of band 14. The enlargement of the distance between opposite ear covering portions 16 permits the ear covering device 10 to be placed on the head of the individual 12, as illustrated in FIG. 1. The spring force created by the flexible band 14 of the ear covering device 10 causes the ear covering portions 16 to engage against the side of the head of the individual 12. The spring force of the band is contemplated to be sufficient to engage the head 12 so that the ear covering device 10 does not fall off. However, the spring force is desired to be limited so that the ear covering device is not uncomfortable to wear.

Figure 3:
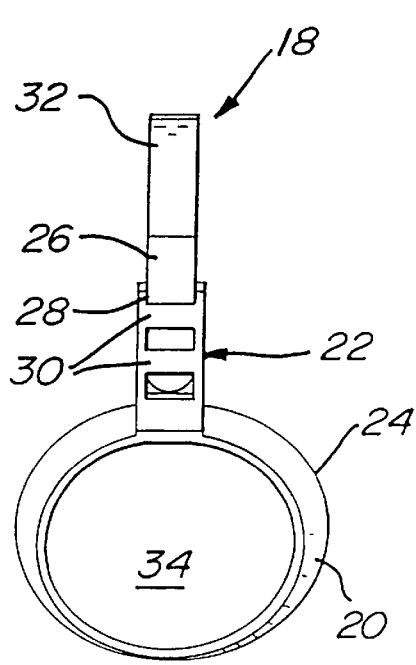
FIG. 3 shows a side plan view of the frame of the covering device of the present invention.
Figure 4:
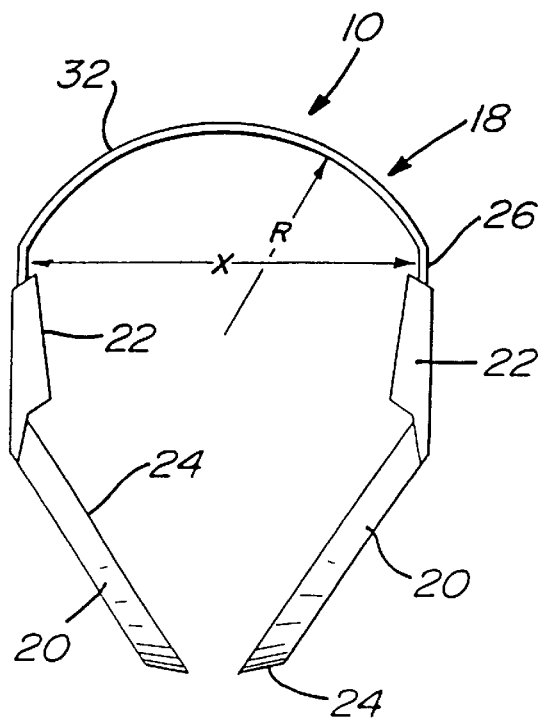
FIG. 4 shows a front plan view of the frame of the covering device of the present invention.
Figure 5:
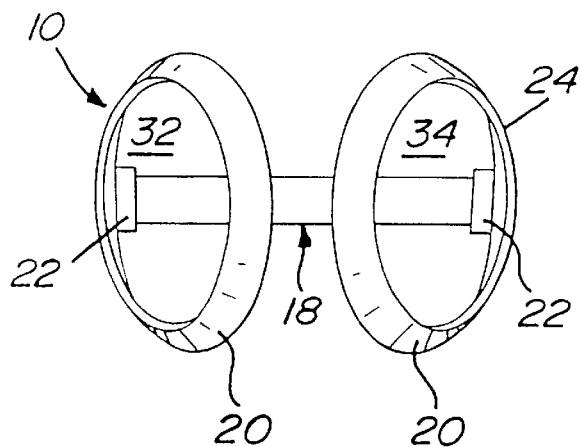
FIG. 5 shows a bottom elevational view of the frame of the covering device of the present invention.

FIGS. 3–5 generally illustrate the framework of covering device 10. The frame generally comprises a flexible band 18 and two ear cup frame members 20. The ear cup frame members 20 include an attachment portion or flange 22 and a frusto conical frame portion 24. The attachment portion 22 in the embodiment illustrated in FIGS. 3–5 is integrally formed with the frusto conical portion 24. The attachment portion 22 is formed at an oblique angle with respect to the plane of the frusto conical portion 24. This angle creates, in part, the inward positioning of the ear covering portions 16 as illustrated in FIG. 2, i.e., position "A". The angle between the attachment flange 22 and the frusto conical portion 24 is contemplated to be in the range of about 90° to 160° and is preferably approximately 145°. The flexible band 18 includes end portions 26 which are engaged within the attachment portions 22 of the ear cup frame members 20. As illustrated in FIG. 3, the end portion 26 is engaged within a slot 28 within attachment portion 22 and is secured therein by ribs 30. A detent (not shown) may be provided on the end portion 26 of the flexible band 18 so as to resist the removal of the ear cup frame member 20 from between the opposing ribs 30 on the end portion 26.

The flexible band 18 as illustrated includes a curved portion 32 and two end portions 26. Preferably, the curved portion 32 has a radius of curvature of approximately 2¼ inches. The end portions are formed by bends at the end of the curved portion 32 and are separated by a distance X, as illustrated in FIG. 4. Preferably, distance X is in the range of about 3.5 to 4.5 inches and specifically about 3.9 inches. The end portions 26 are straight and are formed integral with the curved portion 32. Preferably, the band 18 is made of a stainless steel type material; however, other materials are contemplated, including polypropylene, nylon, polyethylene, etc. The band 18 should be sufficiently flexible such that the relative distance X between the two end portions 26 may be enlarged and the ear cup frame members 20 may be separated prior to placing ear covering device 10 on the individual 12 (FIG. 1).

The ear cup frame members 20 are preferably made of a plastic material, such as nylon. The frusto conical portions 24 at each end of the frame include a central opening 34. The diameter of the frusto conical portion at its base is contemplated to be in the range of about 2.7 to 4 inches and preferably in the neighborhood of 3 inches. The preferred height of the frusto conical portion is in the range of about 0.2 to 0.5 inches. The preferred height dimension if approximately 0.25 inches with the side wall being at an angle of about 45°. The frusto conical portion 24 is contemplated to fit around the ear when wearing of the ear covering device 10.

Figure 6:
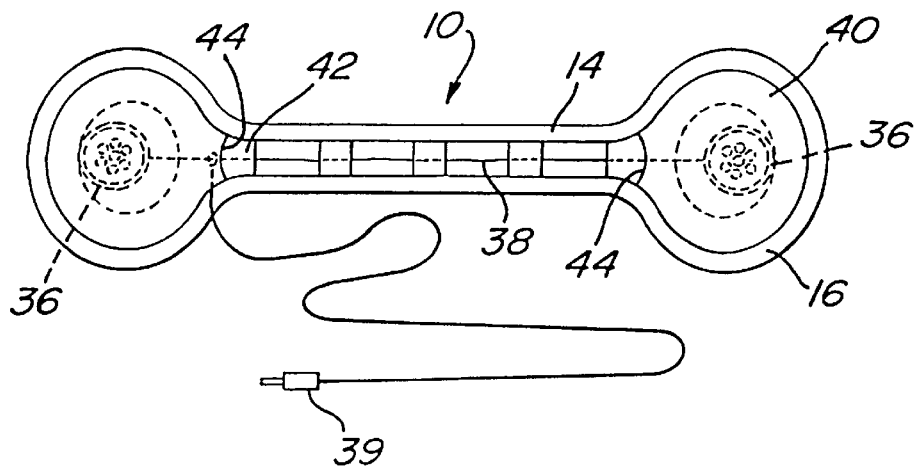
FIG. 6 shows the covering device incorporating a headphone type speaker arrangement therein.

In FIG. 6, the ear covering device 10 is shown having a pair of speakers or earphones 36 and a speaker wire 38 incorporated therein. The earphones 36 and speaker wire 38 are also illustrated in FIG. 7B, separate from the ear covering device 10. The speaker wire 38 terminates in a standard male jack 39 for connection to a personal radio, tape player or the like (not shown).

Figure 7A:
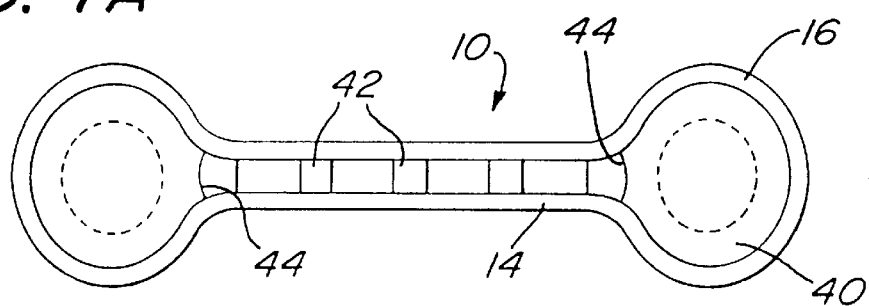
FIGS. 7A and 7B show the component parts of the covering device and headphone speakers as contemplated by FIG. 6.
Figure 7B:
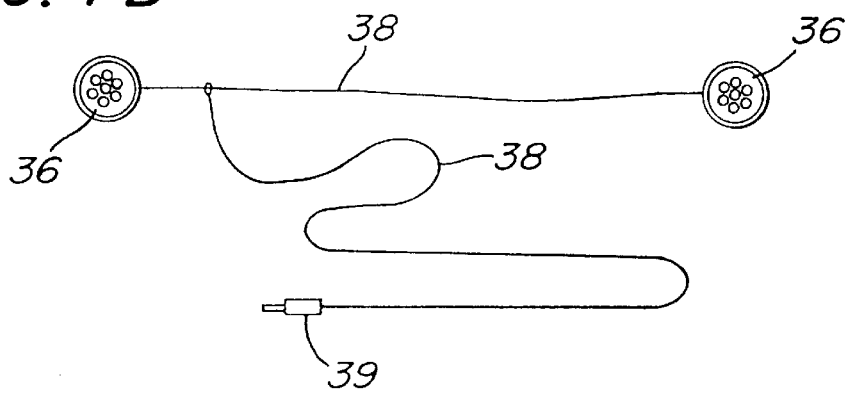

In FIGS. 6 and 7A, the ear covering device 10 includes band 18 and ear cup frame members 20 as shown in FIGS. 3–5. The band 18 and ear cups 20 are covered by a fabric material 40. As illustrated, the band portion 14 and the ear covering portions 16 are each covered with fabric 40. The fabric covering 40 includes a series of bands 42 which engage the speaker wire 38 and retain it within the ear covering device 10. In addition, a pocket is formed within the ear cups 20 which retains the earphones 36. The earphones 36 may be inserted into the pocket by means of slot 44 within the fabric 40. As illustrated, the slot 40 is positioned adjacent to each ear covering portion 16.

Figure 8A:
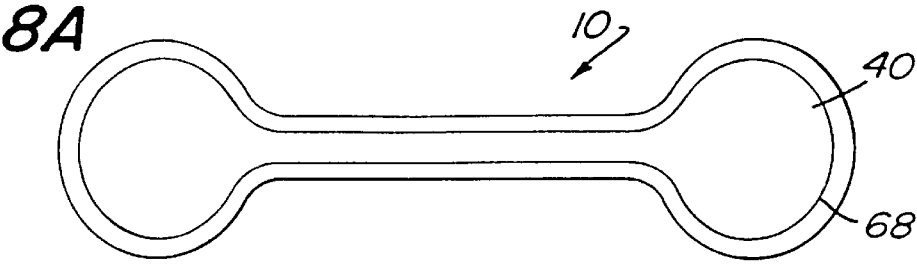
FIGS. 8A through 8F show a series of covering panels which form the fabric covering for the present invention.
Figure 8B:
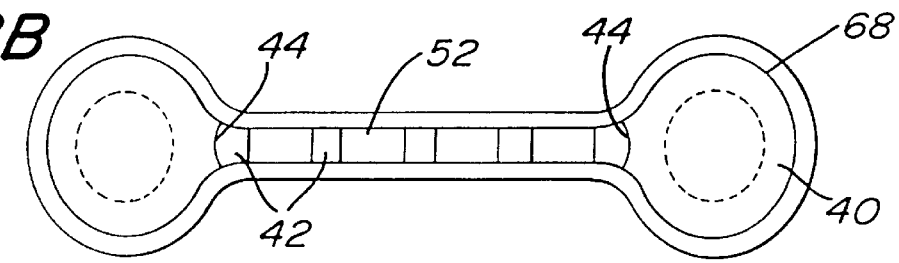

As generally illustrated in FIGS. 8A–8F, the fabric 40 includes multiple layers. In FIG. 8A, there is shown a top plan view of the ear covering device 10 in the open position. The fabric 40 completely covers the outside surfaces of the band 18 and the ear cup frame members 20. As shown in FIG. 8B, the fabric 40 also covers the inside surfaces of the band 18 and ear cups 20.

Figure 8C:
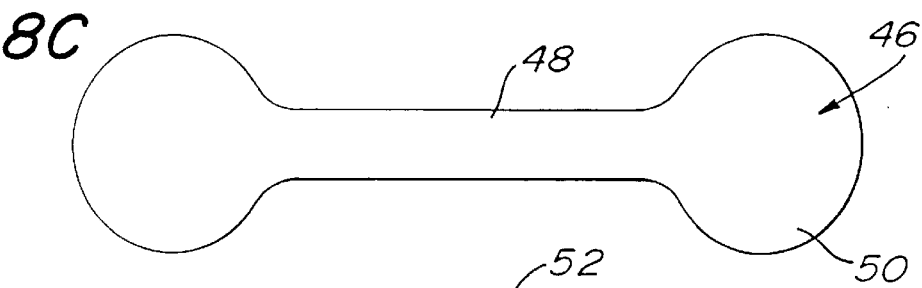
Figure 8D:
Figure 8E:
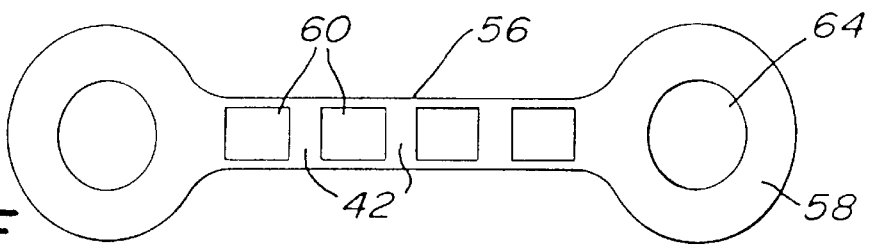
Figure 8F:
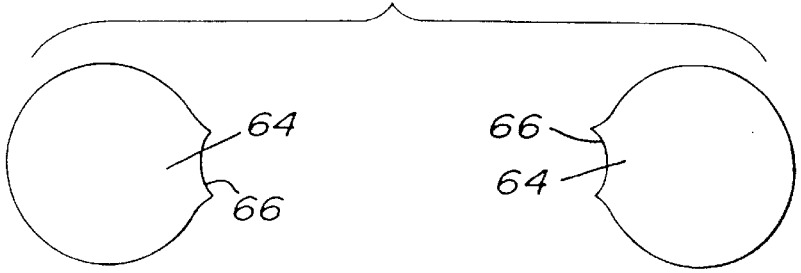

Multiple layers of fabric are utilized to form the fabric covering 40 for the ear covering device 10. These layers are generally illustrated in FIGS. 8C–8F. In FIG. 8C, there is shown an outer shell 46 which includes a central tapered portion 48. In FIG. 8D there is shown an inner fabric covering 52 which when assembled is exposed between bands 42, as shown in FIG. 6. The inner fabric 52 generally covers the inner surfaces of band 18. The inner fabric 52 is overlapped by a central portion 56 which is shown in FIG. 8E. The central portion 56 includes a series of alternating bands 42 and openings 60 in its center and two circular portions 58 at each end. A central opening 62 is provided within the circular portions 58. The central portion 56 is contemplated to be provided on the inside of the ear covering device 10 and at least partially covering the inner fabric 52. Covering the circular portions 58 of the band fabric 56 are inner ear members 64. The inner ear members 64 as shown in FIG. 8F have a generally circular configuration. The inner ear members 64 are positioned over top of the circular portions 58 and the corresponding central opening 62 in central fabric 56. Adjacent one end of the inner ear members 64 is a curved border 66 which in the final constructions forms the slot 44 for insertion of the earphones 36 as contemplated by FIGS. 6 and 7.

The various layers of the fabric material 40 are combined by sewing or the like. The fabric covering may include an outer piping 68. Piping 68 may be formed as part of one of the layers of the fabric material 40 or may be a separate element attached thereto.

Any number of materials are contemplated for the fabric 40. Piping 68 as illustrated in FIGS. 8A and 8B may be a wear-resistant cotton blend or an entirely synthetic material. The exposed outer shell 46 may be a nylon-covered close cell neoprene or other moisture-resistant fabric. The band fabric 54 may also be made of neoprene. Inner central tapered fabric 52 and inner ear members 64 are preferably made of a synthetic fleece type lining material, so as to provide warmth and comfort. The inner ear members 64 will be in direct contact with the individual 12. It is noted that the exposed outer shell 46 may alternatively be made of a fleece material. It has been determined that the fleece material provides sufficient protection from the elements while also permitting sound to pass therethrough.

In FIGS. 9–23, there is illustrated a number of hinge embodiments which may be used to form the connection between the attachment portion 22 and the frusto conical portion 24 of the ear cup frame members 20. Each of these embodiments will be discussed separately below. A number of these embodiments include a living hinge type arrangement. A living hinge as contemplated by the present invention generally includes a continuous plastic formation having a reduced cross-section between a base flange and an attachment flange, wherein flexing is permitted between the two flanges. The form of each of the hinges will be discussed in further detail below.

In FIG. 9, there is illustrated an embodiment of the attachment portion 22' for the ear cup frame member 20'. The frusto conical portion 24 as illustrated in this FIG. 9 is generally contemplated to be the same as that illustrated previously. However, the communication between the frusto conical portion 24 and the attachment portion is not contemplated to be rigid. The living hinge 70 is provided between an attachment flange 72 and a base flange 74. The living hinge 70 permits the ear cup 20 to pivot such that the ear covering portion 16 may collapse into the band portion 14 to reduce the size of the ear covering device 10 when not in use. A rivet hole 76 is provided in the attachment flange 72. The engagement between engagement portion 22' and the flexible band 18 (not shown in FIG. 9) may be made by means of a rivet (not shown). It is contemplated that rotation of the ear cup frame member 20' about the rivet or opening 76 further permits collapsing the ear covering portions 16 into band 14.

In FIG. 10 there is illustrated a further embodiment of the ear cup frame member 20" which includes a frusto conical portion 24 and a modified living hinge 70'. The attachment portion 22' generally includes an inverted T-shaped attachment flange 72' and an L-shaped base flange 74'. The connection between the T-shaped flange 72' and the L-shaped flange 74' forms the living hinge 70' and limits the amount of outward rotation of the frusto conical portion 24 with respect to the attachment portion 22". The hinge 70' permits the inward rotation of the frusto conical portion 24 towards the attachment portion 22" when collapsing the ear covering device 10. Again, a rivet hole 76 is provided in the attachment flange 72' for securing the attachment portion 22" to the end portion of the flexible band 18 (above).

In FIG. 11, there is shown a further embodiment of an ear cup frame member 20'''. In this embodiment, the attachment flange 72" is generally planar with the base flange 74" and includes the hinge 70" positioned therebetween. A slot or groove is provided as part of the living hinge 70" such that a limited amount of inward rotation of the frusto conical portion 24 is permitted with respect to the attachment flange 72". Again, the attachment flange 72" may be secured to band 18 (above) by means of rivet hole 76 and a rivet (not shown).

In FIG. 12 there is illustrated a still further embodiment of an ear cup frame member 20"" including a hinge 70''' formed as part of the attachment portion 22''''. The base flange 74''' in this embodiment generally includes an L-shaped member with one leg of the L-shape being generally planar with the attachment flange 72'''. The living hinge 70''' is provided between the L-shaped flange 74''' and the attachment flange 72''' with the projection of L-shaped flange 74''' serving to prevent full rotation of the frusto conical portion 24 with respect to the attachment flange 72'''.

In FIGS. 13–15, there are illustrated further hinge embodiments for the ear cup frame members. These hinged arrangements are generally contemplated to include a press fit relationship and/or a pin secured within adjacent elements.

In FIG. 13, the frusto conical portion 24 includes a projecting tab 78. Tab 78 includes a rounded end and forms the axis for the hinge 82. Tab 78 is formed integral with the frusto conical portion 24. The securing portion 80 of hinge 82 includes a planar base 81 and a curved projection 84. The curved projection 84 generally encapsulates the end of the projecting tab 78 such as a hinge is formed. The planar base 81 of the securing portion 80 generally limits outward rotation of the frusto conical portion 24. The curve portion 84 may also limit inward rotation about the hinge 82.

In FIG. 14, the frusto conical portion generally includes a projecting tab 78' which includes a central slot. A tab 86 on the securing portion 88 is engaged within the slot in tab 78. A pin 90 forms an axis for the hinge and extends through the ends of tabs 78 and 86.

In FIG. 15 there is shown a further embodiment of a hinge construction for the ear cup frame. The frusto conical portion 24 includes two projections 92 which are formed on the inside surface of the cone 24. The base members 92 engage on opposite sides of a projecting tab 86' which is formed as part of the securing portion 88. A pin (not shown) forms the axis for the hinge and extends through the projections 92 and the tab 86' on securing portion 88.

Figure 16:
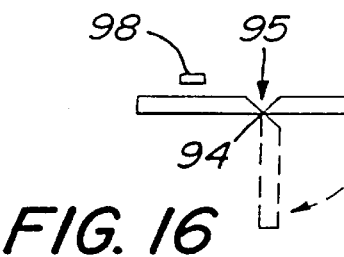
FIGS. 16 through 24 show side elevational views of various embodiments of a "living hinge" for use within the covering device of present invention.

In FIG. 16 there is illustrated a living hinge in the form similar to that shown in FIG. 11. The hinge 94 generally includes a V-shaped notch 95 within a planar body portion 96. Projecting from the left hand element of the planar body portion 96 is an attachment head 98 which may be inserted into an opening in the end portion 26 of band 18 (not shown). It is contemplated that the press fit relationship between the opening in end portion 26 and the attachment head 98 will form a pivot similar to the rivet attachment contemplated for the embodiments in FIGS. 9–15. In phantom, there is illustrated the flexing of the living hinge 94.

Figure 17:
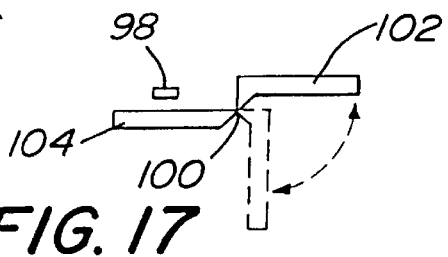

In FIG. 17, a further embodiment of the living hinge is shown. The hinge 100 is formed between a first base member 102 and a second base member 104. The second base member 104 includes an attachment head 98, similar to that contemplated by FIG. 16. However, in this embodiment, the first base member is not planar with the second base member 104. The flexing of the hinge 100 is shown in phantom.

Figure 18:
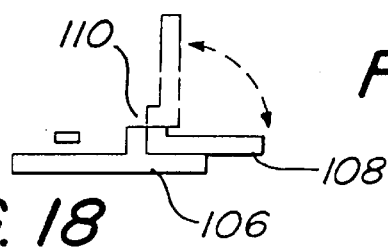

In FIG. 18, there is illustrated a living hinge having a form similar to that shown in FIG. 10 above. A first base member 106 forms an inverted T-shaped element and is provided along with an L-shaped base member 108. The hinge 110 is formed between the first and second base numbers 106. 108. Because of the projecting portion on the right hand side of the first base member 106 (as illustrated in FIG. 18) the downward rotation of the second base member 108 is limited. The movement of the second base member 108 is shown in phantom.

Figure 19:
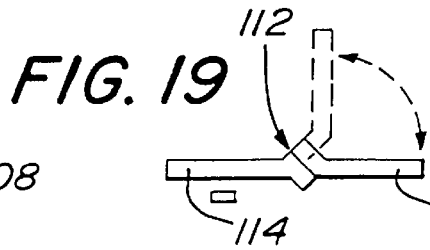

In FIG. 19, there is a shown a still further embodiment of a living hinge type attachment for the ear cup member. The hinge 112 is formed between a first base member 114 and a second base member 116. The first and second base members 114, 116 each include a bend at their respective ends which permit the formation of the hinge 112. The bent ends engage one another so as to limit rotation of second base member 116 in the downward direction (as shown). The rotation of member 116 in the upward direction is shown in phantom.

Figure 20:
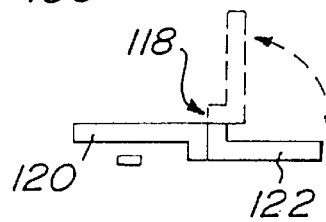

In FIG. 20, there is a further embodiment of a living hinge type structure. In this embodiment, the hinge 118 is formed between two L-shaped members 120 and 122. The L-shaped members are positioned opposite one another, such that their elongated projections are not planar. This arrangement again limits downward rotation of the right hand L-shaped member 122. The upward rotation of member 122 is shown in phantom in this FIG. 20.

Figure 21:
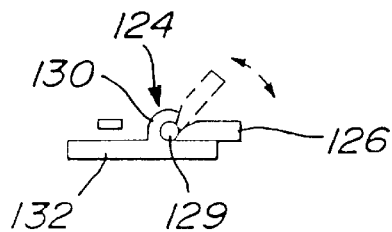

In FIG. 21, there is illustrated a hinge arrangement similar to that contemplated by FIG. 13 above. The hinge 124 is formed by a tab 126 having a circular end 128 which is engaged within a curved projection 130 formed on a planar member 132. The tab 126 engages the upward surface of planar 132 so as to limit rotation thereof downwardly about the hinge 124. In addition, the upward rotation of tab 126 about the hinge 124 is limited as illustrated in phantom. The upper surface of tab 126 engages the end the of curved portion 130. The hinge 124 is contemplated to be formed by a press fit relationship between the rounded end 128 of tab 126 and the inside surfaces of curved projection 130.

Figure 22:
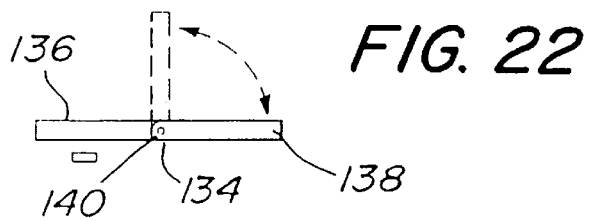

In FIG. 22, there is illustrated a further embodiment of a hinge which is generally similar to that shown in FIG. 14. The hinge 134 is formed between a first member 136 and a second member 138. It is contemplated that the first and second member include engaging projections which are formed around a central pin 140. The upward rotation of second member 138 about the hinge 134 is shown in phantom.

Figure 23:
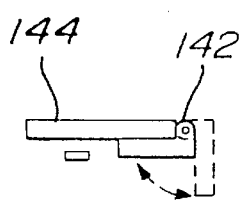

In FIG. 23, there is illustrated a further embodiment of a hinge connection. The hinge 142 is formed between a first planar member 144 and an L-shaped second member 146. The L-shaped second member 146 permits the upper surface of the second member 146 to engage the lower surface of the first planar member 144 when the hinge 142 is collapsed. The opening of hinge 142 is shown in phantom.

Figure 24:
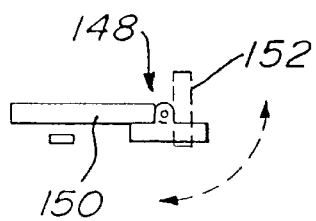

In FIG. 24, there is illustrated a further hinge embodiment. The hinge 148 is formed between a first planar member 150 and a T-shaped second member 152. The hinge is formed on the central portion of the T-shape in a manner similar to that contemplated by the hinge 134 in FIG. 22 and the hinge 142 in FIG. 23. Again, the upper portion of the T-shaped member 152, when in inverted position, engages the lower surface of the planar member 150 to limit rotation about the hinge 148. The rotation of hinge 150 is illustrated in phantom.

Figure 25:
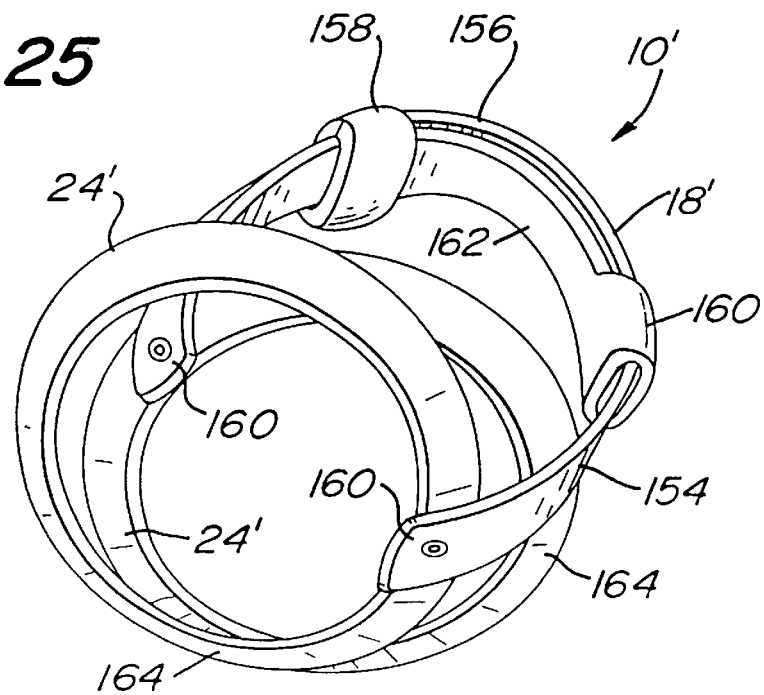
FIG. 25 shows a collapsible frame for an ear covering device.
Figure 26:
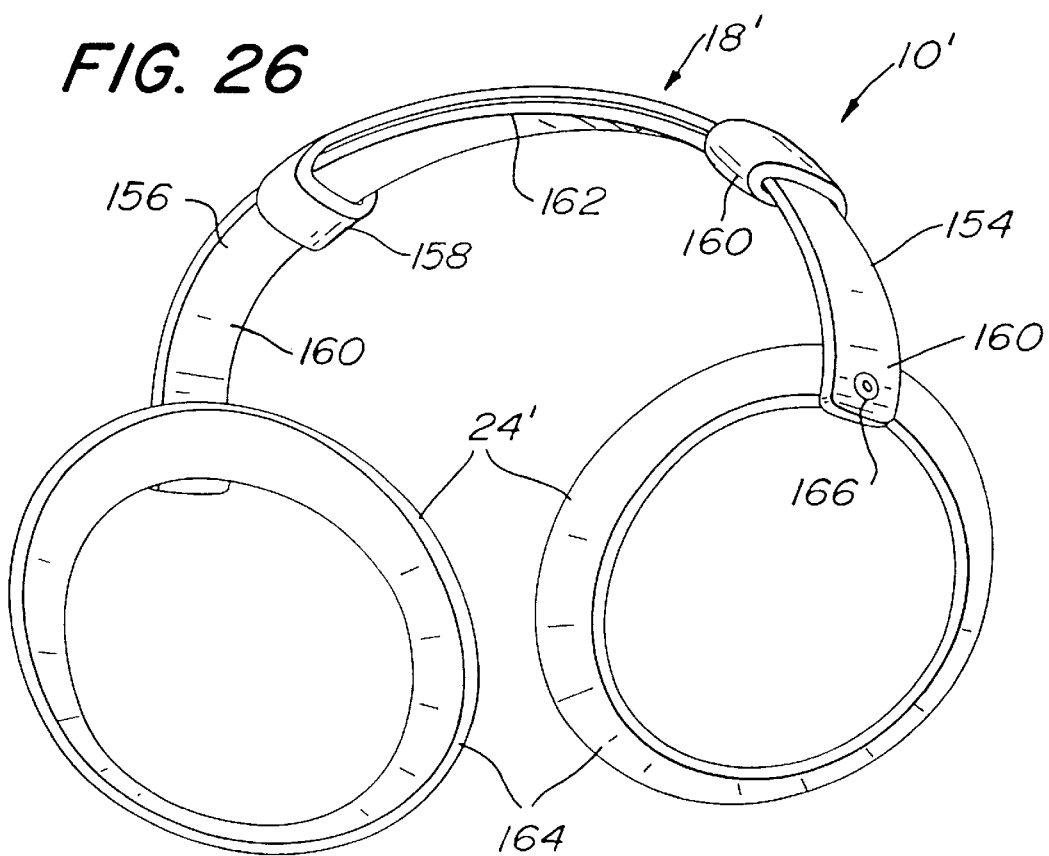
FIG. 26 shows the collapsible frame of FIG. 25 illustrated in an opened position.
Figure 27:
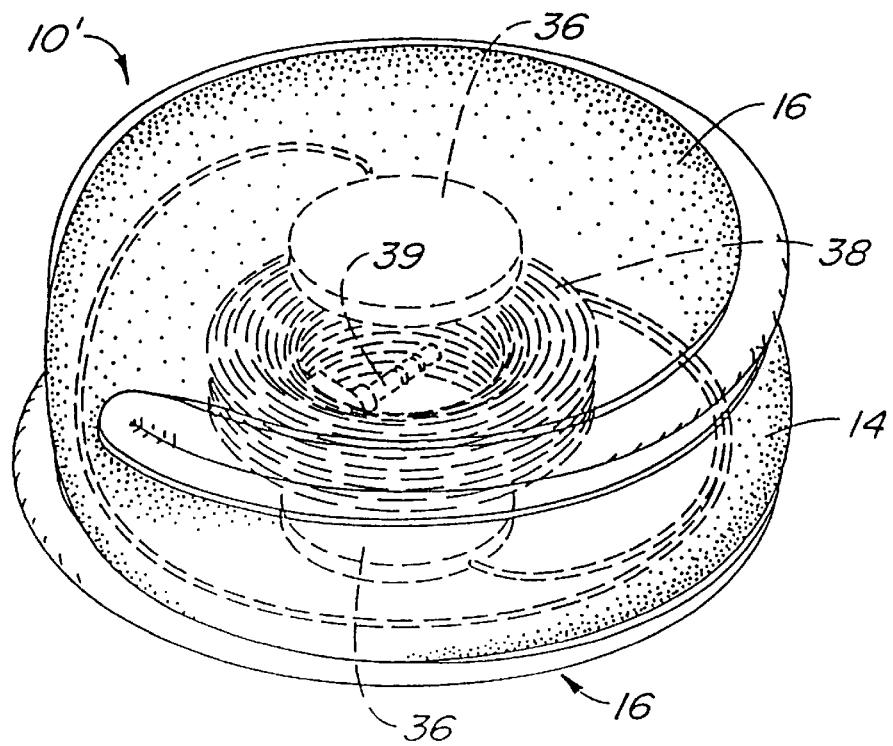
FIG. 27 shows an ear covering device in accordance with the present invention, illustrated in the collapsed position.

In FIGS. 25, 26 and 27, there is illustrated a collapsible ear protection device 10' which is shown in the open position (FIG. 26) and in the closed position (FIGS. 25 and 27). For illustrative purposes, only the frame portion of the ear protection device 10' has been shown in FIGS. 25 and 26. However, a fabric covering similar to the embodiment shown in the figures discussed above is contemplated to be included and is shown in FIG. 27.

The band 18' of device 10' generally includes a semi-circular first portion 154 and a semi-circular second portion 156 which engage one another to form a continuous arc. Engagement is formed by wrapping a portion of each member 156 and 154 around the other. The wrapping portion of the first semi-circular portion 154 is identified by the numeral 158. The wrapping portion of the second semi-circular member 156 is identified by the numeral 160. As an alternative to wrapping the two portions around one another, separate rings or bands may be wrapped around one end of the first member 154 (for example) and attached thereto. The rings will also be wrapped around the central portion of the second member 156. In final assembly, as illustrated in FIG. 26, the end of the band 18' identified by the numeral 160, includes a single layer whereas the central portion 162 of the band 18' includes an overlapped double layer. The double layer portion may be shortened or elongated by sliding the two members 154 and 156 with respect to one another so as to move the wrapping portions 158 and 159 closer together. To shorten the overall length of the band 18' the two wrap portions 158 and 159 are moved further apart from one another (elongating the overlap 162 of the two portions, but shortening the overall length of the band 18').

In FIGS. 25 and 26, the frusto conical portion 24' forms the entirety of the ear cup 164. The connection between the ends 160 of the band 18' is preferably formed by an attachment head 166, similar to that specifically illustrated in FIG. 16 (element 98; also illustrated in FIGS. 19–22), and a socket or opening in the ends 160 of the band 18'. As illustrated, the attachment head is inserted in the opening in a press fit type relationship. Alternatively, the ends 160 could include an inverted V-shaped notch with a rounded opening at the top. The shaft of the attachment head in this contemplated embodiment would be slid into the notch and retained within the rounded opening, again in a press fit type relationship. Another possibility is a "figure 8" type opening with one side thereof being larger than the other. In this form, the enlarged diameter of the head portion can be inserted into the larger opening and then the shaft portion slid into the smaller portion of the opening (again in a press fit relationship). Other forms of detachable fastening and non-detachable fastening (such as a rivet) are contemplated.

The intent of this type attachment is to permit the frusto conical portion 24' to rotate about the attachment head 166 and the end of the band 18'.

As is more particularly illustrated in FIG. 27, one frusto conical portion 24' formed within the ear covering portion 16' may be rotated so as to flatten against the opposite ear covering portion 16' (which is also rotated) with the central portion 14 (which covers band 18') forming a circular (or at least semi-circular) side wall between the parallel ear covering portions. In this manner, the collapsed ear covering device 10' can retain the speaker wire 38 and male jack 39 (each shown in phantom). The speakers 36 (also shown in phantom) are retained within the ear covering device within the pocket formed by the central opening 62 within the central fabric portion (FIG. 8E) and the respective outer shell 46 (FIG. 8C) and inner ear members 64 (FIG. 8F).

Figure 28:
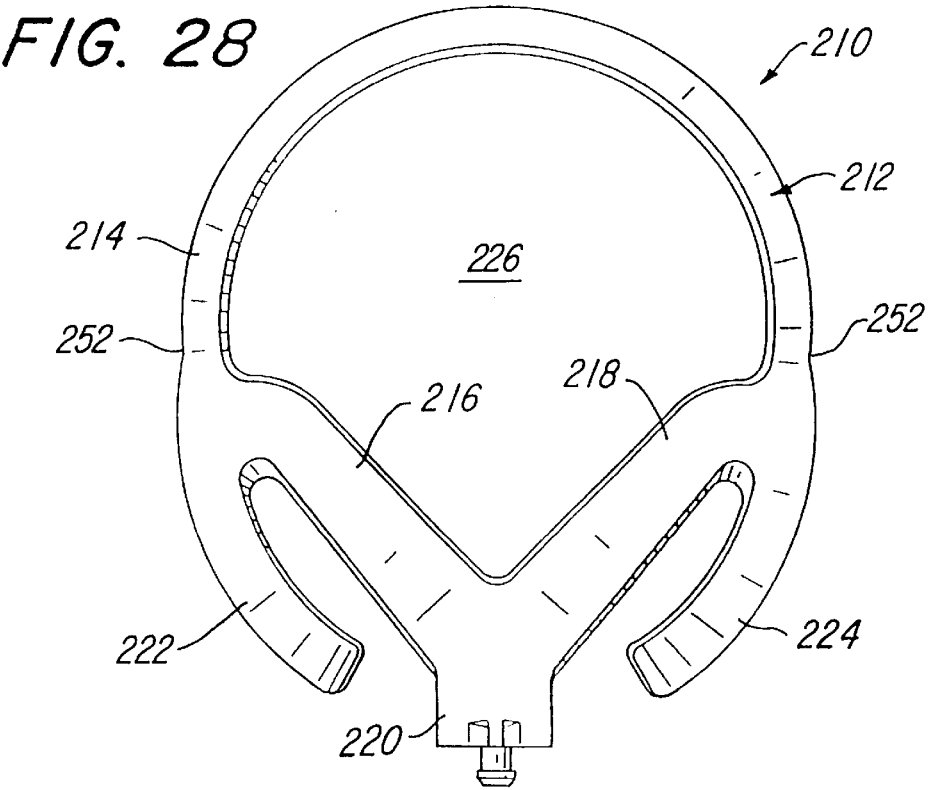
FIG. 28 is a top plane view of a portion of an alternate embodiment of an ear covering device as contemplated by the present invention.

In FIGS. 28–38, there is shown an alternate embodiment of a frame for an ear protection device. The frame of this embodiment is generally labeled with the numeral 210. In FIGS. 28 and 29, there is particularly illustrated an ear cup frame member 212. The ear cup frame 212 includes a modified ear cavity having a semi-circular frame 214 at one end, two support flanges 216, 218 formed as a central V-shaped portion, an attachment portion or flange 220, and two cup extension portions 222 and 224. The modified ear cavity is generally shown in FIG. 28. The semi-circular portion 214 defines, along with the support flanges 216, 218, a central opening 226. The attachment flange 220 extends outwardly from the vertex of the V-shape of the support flanges 216, 218.

As illustrated more particularly in FIGS. 29 and 30, the outline of the cavity of ear cup 212 is generally formed by the cup extensions 222, 224, along with the semi-circular frame portion 212. The support flanges 216, 218 project above the ear cup to further define the cavity for receiving an ear. Thus, the frame member 212 forms a open area defined by the height of the semi-circular portion 214 and the cup extensions 222 and 224, as well as the projection of the support flanges 216, 218 there above.

As shown in FIG. 30, the frame 210 includes a band 230 which is comprised of a first curved portion 232 and a second curved portion 234. The two band portions 232, 234 overlap and engage one another by means of passageways 236, 238. Passageway 236 is positioned at one end of band portion 234, which is opposite band end 228. Passageway 238, formed as part of the band portion 232, is positioned at the opposite end of band 234 from attachment end 226. Band portion 232 on its inside surface includes a series of raised bumps or ratchet teeth 240 which form a resistance to the sliding movement of passageway 236 of band portion 234 when the expansion of the overall length of the band 230 is desired. The passageways 236 and 238 include a lower portion in which the opposing band slides. As can be seen, the thickness of the band ends 226, 228 increases in the area of the openings 246, 248. An upper portion is included in the passageways which permits the passage of the passageway 236 over the end 226 of band portion 232 and, similarly, the passage of passageway 238 over the band end 228 of band portion 234. Each band end 226 and 228 includes a projecting tab 242 and 244, respectively, which extends beyond the openings 246 and 248, respectively, which receive the attachment head 250 of the two ear cup frame members 212.

The connection between the attachment head 250 and the openings 246 and 248 in the band portions 232 and 234, respectively, permits the rotation of the ear cup around the axis of the attachment head 250. When the band ends 226, 228 are aligned with the attachment flange 220, the tabs 242, 244 form a moment arm which translates the spring force, created by the curvature of the band 230, to the ear cup frame members. This permits the ear cup frame member to flex and engage around the ear of the wearer. The semicircular portion 214 flexes with respect to the more rigid structure of the support flanges 216, 218 due to the "twist" line created by the relief area 252 on opposite sides of the ear cup frame 212. In addition, the attachment flange 220 is provided with raised bumps 254 on the outside surface thereof. The raised bumps define a slot therebetween in which is engaged a bump 256 on the inside surface of band end 242 of band portion 232 or a bump 258 on end 228 of band portion 234. The engagement of bumps 256, 258 within the slot formed by the raised portions 254 on attachment flange 220 secures the ear cup frame member 212 in alignment with band 230. This engagement can be overcome by a slight rotation of the ear cup 212 with respect to the band 230.

Figure 31:
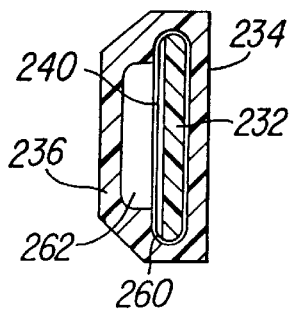
FIGS. 31–38 show various features of the alternate frame embodiments as shown in FIG. 30.

In FIG. 31 there is shown a cross section of the engagement of band portion 232 by passageway 236 on the end of band portion 234. As discussed above, the passageway 236 includes a first slot portion 260 in which in engaged the main part of band portion 232. A second slot portion 262 is also provided within the passageway 236, for passage of the enlarged or thickened portion of the end 242 of the band 232.

Figure 33:
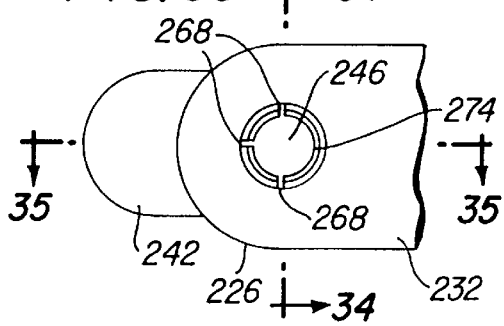
Figure 34:
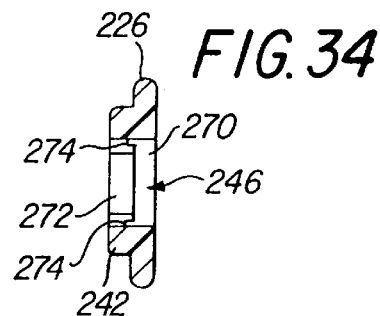
Figure 35:
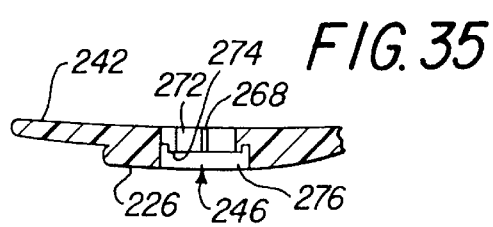

The end 242 of band 232 is shown in more detail in FIGS. 33–35. Projecting tab 242 extends outwardly from the end 226 of the band portion 232. The extension of tab 242 created an additional moment about the engagement of the attachment head 250 (FIGS. 29–30) within the opening 246. As shown in FIG. 33, the tab 242 has a lesser width than the main portion of the band 232. As shown in FIGS. 34 and 35, the tab 242 is formed integral with the band end 226 and projects from its lower or inside surface. Thus, the thickness of the band 232 adjacent the opening 246 is greater than the remaining band portions. However, the thickening of the end 226 of the band portion 232 created by the tab portion 242 is restricted in width. This width restriction is provided so that the end 226 of the band portion 232 can be inserted during assembly through the passageway 236 of the opposite band portion 234. Tab portion 242 passes through the second slot portion 262 while the main portion of band 232 passes through first slot portion (FIG. 31) so as to form the overlap by the band portion 234. The difference in width permits the overlap to remain secure, without excessive movement of the band portion 232 within the passageway 236. In addition, the edges of the first slot portion 260 within passageway 236 serve to engage the ribs 240 on the inside surface of band portion 232.

Figure 32:
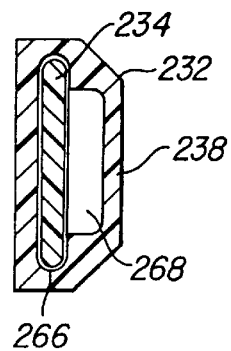

In FIG. 32 there is shown in cross section the passageway 238 on band portion 232 in engagement with band portion 234. Passageway 238 is formed similar to passageway 234 on the one end of band portion 234. The main portion of band 234 is positioned within a first slot portion 266. A second slot portion 268 is formed adjacent the first slot portion 266, to provide passage for the thickened portion of the end 244 (discussed in further detail below).

Figure 36:
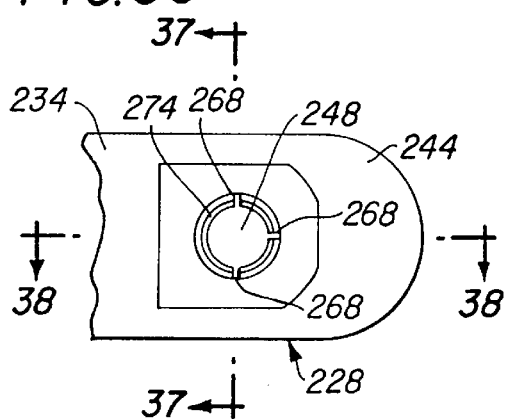
Figure 37:
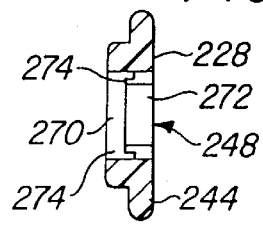
Figure 38:
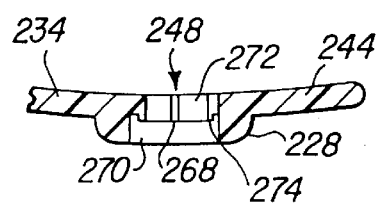

In FIGS. 36–38, there is shown the structure of the end 244 of the band portion 234 which is attached to the ear cup frame member 212. On the end 244 of the band portion 234, a raised area is provided adjacent the opening 248 for receipt of the attachment head 250 (FIGS. 28–30). As can be seen more particularly in FIGS. 37 and 38, the raised area surrounds the opening 248 and has a width which is less than the width of the main portion of band portion 234. This step in the thickness of the band portion permits the passage of the end 244 of the band portion 234 through passageway 238 (FIG. 32) during assembly. In particular, the raised area of the band end 244 passes through the second slot portion 266 within the passageway 238.

The openings 246 and 248 within the respective band ends 242 and 244 are formed by a central circular hole having three radially projecting slots 268 extending outwardly therefrom. As shown in the cross sections of FIGS. 34–35 and 37–38, each opening 246, 248 includes an upper chamber 270 and a lower chamber 272. The upper chamber 270 has a diameter that is greater than the lower chamber 272. The radially extending slots 268 project outwardly from the lower chamber 272. In addition, a rib 274 is formed around the circumference of the opening which forms the lower chamber 272. The rib 274 projects into the upper chamber 272 within openings 246 and 248. The rib 274 is discontinuous, in that the slots 268 extend through the rib 274 in addition to the side walls of the lower chamber 274.

As seen in FIG. 30, the attachment head 250 includes a shaft which is connected at one end to the attachment flange 220 portion of the ear cup frame member 212. The shaft is enlarged at the projected end of the attachment head 250. The attachment heads 250 of separate ear cup frames 212 are inserted into the openings 246, 246 in the ends 242, 244 of the two band portions 232, 234, respectively. The opening of the lower chamber 272 has a diameter which is slightly larger than the diameter of the shaft of the attachment head 250, so as to permit the ear cup frame member 212 to rotate about the axis of the shaft. The enlarged end of the attachment head 250 has a diameter greater than the opening formed by the lower chamber 272. The enlarged end is pressed through the lower chamber opening 272 and fits within the upper chamber 270. The radial slots 268 permit the side walls of the lower chamber 272 to flex during the insertion of the attachment head 250 into the openings 246, 248. The press fit relationship between the attachment head 250 and the openings 246, 248 secures the ear cup frame members 212 to the ends of the band 230. The slots 268 provide flexibility to the side walls of the lower chamber 272 within the openings 246, 248 and facilitate the creation of the press fit attachment. The ribs 274 engage the lower portion of the enlarged end of attachment head 250. The rib 274 limits the axial movement of the attachment head 250 within the openings 246, 248. Also, the 180° portion of the rib 274 that extends between two of the slots 268 is positioned on the side of the openings 246, 248 opposite of the projected ends 242, 244, respectively. This arrangement stabilizes the engagement of the attachment head 250 within the openings 246, 248 and limits play between the band 230 and the ear cup frame members 212.

The overall structure of the embodiment shown in FIGS. 28–38, is contemplated to be generally larger than those shown in the earlier embodiments. In addition, the cavity of the ear cup frame member 212 is contemplated to have a more semi-circular interior due to the inclusion of the support flanges 216 and 218 and due to their relationship with the attachment flange 220.

The frame embodiment 210 shown in FIGS. 28–38, is contemplated to include a fabric covering similar to those discussed above. In addition, speakers, such as those shown in FIGS. 6, 7b and 27, may be included within the interior of the ear covering device 210.

The frame of this or any embodiment may be made of a Crastin® material which is manufactured by the DuPont Company. The Crastin® material is considered less susceptable to changes in moisture than a typical nylon material and is not severely effected by changes in temperature. It is contemplated that the characteristics of this material and its higher flex modulus will enable the frame to be relatively thinner than would be possible by a the use of nylon material, while still accomplishing the desired characteristics of the present invention.

The present invention may be embodied in other specific forms without departing from the spirit or essential attributes thereof and, accordingly, reference should be made to the appended claims, rather than to the foregoing specification, as indicating the scope of the invention.

We claim:

1. A covering device to be worn over the ears of an individual and extend around the back of the individual's head, comprising:

a flexible band, the band having a central curved portion and two end portions, the band having an inner side facing towards the individual and having an outer side facing away from the individual;

two ear cups, one ear cup attached to each end portion of the band, at least a portion of the ear cups having a frusto conical configuration and a central opening therein, each ear cup having an inner side facing towards the individual and having an outer side facing away from the individual; and a plurality of fabric layers covering at least the frusto conical portion of the ear cups, the central opening and the flexible band, the fabric layers covering both the inner side and the outer side of the flexible band and covering both the inner side and the outer side of the two ear cups, the fabric layers being sewn with a single seam, the fabric layers and the ear cups forming a pocket in the fabric layers for insertion of an earphone into the pocket.

2. The ear covering device as claimed in claim 1, wherein the fabric layers include an elastic layer having alternating bands and openings.

3. The ear covering device as claimed in claim 1, wherein the ear cups are hingedly connected to the end portions of the band.

4. The ear covering device as claimed in claim 1, wherein the hinge connection between the end portions and the band is formed by a living hinge.

5. A covering device to be worn over the ears of an individual and extending around the back of the individual's head or neck, comprising:

a band having a central curved portion and two straight end portions, the curved portion having a radius of curvature of about 2¼ inches, two ear cups each having an attachment flange and a base flange, each ear cup attached to the opposite end portions of the band, the attachment being formed by the attachment flange including a hinge for at least partial rotation of the frusto conical cup portion about the attachment flange, the hinge including a continuous plastic formation having a reduced cross-section between the flange and the attachment flange so that flexing is permitted between the base flange and the attachment flange, a frusto conical cup portion having a central opening therein, the attachment flange integrally formed with the frusto conical cup portion at an oblique angle thereto, the frusto conical cup portion defining a frusto conical cavity, and the curvature of the central portion of the band and the oblique angle of the attachment flange with the frusto conical cup portion directing the ear cups inwardly towards one another from opposite sides of the band.

6. The covering device as claimed in claim 5 further comprising: earphone means integrated within the ear cups, the earphone means positioned within the central opening of the frusto conical portion and covered by the fabric means.

7. A covering device as claimed in claim 5 further comprising: a pair of speakers, each speaker positioned within the central opening of the frusto conical portion of the ear cup, and a speaker wire connected to the speakers and at the opposite end to a standard male jack.

8. A covering device as claimed in claim 7, wherein a portion of the speaker wire is retained within the fabric means covering the central curve portion of the band.

9. A covering device as claimed in claim 5, wherein the formation of the attachment flange with the frusto conical cup portion include a hinge for at least partial rotation of the frusto conical portion about the attachment flange.

10. A covering device as claimed in claim 9, wherein the hinge is a living hinge.

11. A covering device as claimed in claim 10, wherein the hinge connection between the attachment flange and the frusto conical portion includes means for limiting the rotation of the frusto conical portion about the attachment flange.

12. A covering device as claimed in claim 5, wherein the attachment of the ear cups to the opposite end portions of the band is formed by an attachment head, the attachment head forming a rotational pivot for the ear cups with respect to the ends of the band such that the ear cups may rotate about the axis of the attachment head.

13. A covering device to be worn over the ears of an individual and extending around the back of the individual's head or neck, comprising:
a band having a first curved portion and a second curved portion, one end of each of the first and second curved portions overlapping and slidably attached to opposing curved portion, such that the relative overall length of the band may be adjusted,
two ear cups, one ear cup attached to the free end of the first curved portion and the second ear cup attached to the free end of the second curved portion, the ear cups defining a cavity formed from two support flanges, formed in a V-shape, and a semi-circular frame portion which extends between opposite projections of the V-shape of the flanges, the semi-circular portion and the support flanges defining a central opening, an attachment flange projecting from the vertex of the support flanges in a direction opposite the semi-circular portion, the attachment flange including means thereon for rotatably attaching the ear cups to the free ends of the first and second curved portions, and
fabric means covering the band and the ear cups on both sides thereof and forming a pocket within the cavity of the ear cups.

14. A covering device as claimed in claim 13, wherein the ear cups further comprise two cup extensions projecting from the projected ends of the V-shaped support flanges in a direction opposite of the semi-circular frame portion.

15. A covering device as claimed in claim 13, wherein the attachment means for the ear cups further comprises an attachment head which projects from the outer surfaces of the attachment flange, the attachment head forming a pivot for the ear cups with respect to the free end of the band portions upon which it is attached, the attachment permitting rotation of the ear cups about the axis of the attachment head.

16. A covering device as claimed in claim 15, wherein the attachment head is snap-fit within an opening in the end of the band portion.

17. A covering device as claimed in claim 13, wherein the first curved portion of the band includes a series of raised bumps on the interior surface thereof which engage the overlap formed by the second band portion to form a resistance to the relative sliding movement of the two band portions when adjustment of the overall length of the band is desired.

18. A covering device as claimed in claim 13, wherein the fabric means is constructed from a plurality of fabric pieces sewn with a single seam.

19. A covering device as claimed in claim 13, wherein the two ear cups rotatably engage into a position at the free ends of the first and second curved portions so that the ear cups are aligned with the band.

20. A covering device as claimed in claim 13, wherein:
a section adjacent to the end of the first curved portion of the band is less wide than the end of the first curved portion of the band, and
a section adjacent to the end of the second curved portion of the band is less wide than the end of the second curved portion of the band.

21. A covering device as claimed in claim 13, wherein the band and the two support flanges direct the ear cups inwardly towards one another to maintain position of the covering device.

22. A covering device as claimed in claim 21, wherein the covering device retains the position around the back of the individual's head or neck without any support around the top of the individual's head.

23. An ear warmer frame, comprising:
a band having;
a first curved portion having an enlarged portion at a first end and a passageway at a second end, and
a second curved portion, having an enlarged portion at a first end and a passageway at a second end,
each passageway having a first slot portion allowing the opposite curved portion of said band to slide through and having a second slot portion allowing the enlarged portion of the opposite curved portion of said band to slide through,
whereby one end of each of the first and second curved portions overlapping and slidably attached to opposing curved portion, such that the relative overall length of the band may be adjusted.

24. The ear warmer frame of claim 23, further comprising:
two ear cups each having an attachment head, each attachment head attaching to one enlarged portion of one curved portion of said band.

25. The ear warmer frame of claim 23, wherein the passageway of the first curved portion said band is integrally formed with the first curved portion of said band, the passageway of the second curved portion said band is integrally formed with the second curved portion of said band.

26. The ear warmer frame of claim 23, wherein the first curved portion of the band includes a series of raised bumps on the interior surface thereof which engage the overlap formed by the second band portion to form a resistance to the relative sliding movement of the two band portions when adjustment of the overall length of the band is desired.

* * * * *

UNITED STATES PATENT AND TRADEMARK OFFICE
CERTIFICATE OF CORRECTION

PATENT NO. : 5,835,609
DATED : November 10, 1998
INVENTOR(S) : Brian E. LeGETTE et al.

It is certified that error appears in the above-indentified patent and that said Letters Patent is hereby corrected as shown below:

In the Title Page [63]: Change "450,587" to --460,587--.

| Column | Line | |
|---|---|---|
| 2 | 4 | Change "a earphone" to --an earphone--. |
| 2 | 23 | Change "including" to --includes--. |
| 2 | 65 | Before "present" insert --the--. |
| 3 | 19 | Change "there is shown" to --there are shown--. |
| 4 | 18 | Change "integral" to --integrally--. |
| 4 | 35 | Change "dimension if" to --dimension is--. |
| 4 | 38 | Delete "wearing of". |
| 4 | 39 | After "10" insert --is worn--. |
| 5 | 42 | Change "there is illustrated" to --there are illustrated--. |
| 6 | 8 | Change "portion 22'" to --portion 22"--. |
| 6 | 47 | Change "formed integral" to --formed integrally--. |

UNITED STATES PATENT AND TRADEMARK OFFICE
CERTIFICATE OF CORRECTION

PATENT NO. : 5,835,609
DATED : November 10, 1998
INVENTOR(S) : Brian E. LeGETTE et al.

It is certified that error appears in the above-indentified patent and that said Letters Patent is hereby corrected as shown below:

| Column | Line | |
|---|---|---|
| 7 | 30 | Change "there is a shown" to --there is shown--. |
| 7 | 53 | After "planar" insert --member--. |
| 7 | 56 | Change "end the of curved" to --end of the curved--. |
| 7 | 64 | Change "second member" to --second members--. |
| 8 | 45 | After "band 18'" insert --,--. |
| 9 | 1 | Change "type attachment" to --type of attachment--. |
| 9 | 40 | Change "there above" to --thereabove--. |
| 10 | 23 | Change "in which in" to --in which is--. |
| 10 | 30 | Change "created" to --creates--. |
| 10 | 44 | Before "first" insert --the--. |
| 11 | 25 | Change "246, 246" to --246, 248--. --. |
| 11 | 66 | Change "suspectable" to --susceptible--. |
| 12 | 4 | After "by" delete "a". |

UNITED STATES PATENT AND TRADEMARK OFFICE
CERTIFICATE OF CORRECTION

PATENT NO. : 5,835,609

DATED : November 10, 1998

INVENTOR(S) : Brian E. LeGETTE et al.

It is certified that error appears in the above-indentified patent and that said Letters Patent is hereby corrected as shown below:

| Column | Line | |
|---|---|---|
| 12 | 41 | Change "claim 1" to --claim 3--. |
| 12 | 57 | Before "flange" insert --base--. |
| 13 | 15 | Change "include" to --includes--. |
| 14 | 34 | After "having" change ";" to --:--. |
| 14 | 46 | After "portions" insert --is--; change "opposing" to --the opposite--. |
| 14 | 53 | After "portion" insert --of--. |
| 14 | 55 | After "portion" insert --of--. |

Signed and Sealed this

Twenty-third Day of November, 1999

Attest:

Q. TODD DICKINSON

*Attesting Officer*      *Acting Commissioner of Patents and Trademarks*